United States Patent
Bollenbeck

(10) Patent No.: US 9,813,149 B2
(45) Date of Patent: Nov. 7, 2017

(54) METHOD FOR COMMUNICATING IN A MAGNETIC RESONANCE APPARATUS AND MAGNETIC RESONANCE APPARATUS OPERATING THEREWITH

(71) Applicant: Siemens Aktiengesellschaft, Munich (DE)

(72) Inventor: Jan Bollenbeck, Eggolsheim (DE)

(73) Assignee: Siemens Aktiegesellschaft, Munich (DE)

( * ) Notice: Subject to any disclaimer, the term of this patent is extended or adjusted under 35 U.S.C. 154(b) by 0 days.

(21) Appl. No.: 14/991,166

(22) Filed: Jan. 8, 2016

(65) Prior Publication Data
US 2016/0204860 A1 Jul. 14, 2016

(30) Foreign Application Priority Data
Jan. 9, 2015 (DE) .......................... 10 2015 200 214

(51) Int. Cl.
*H04B 10/00* (2013.01)
*H04B 10/116* (2013.01)
*A61B 5/055* (2006.01)

(52) U.S. Cl.
CPC ............ *H04B 10/116* (2013.01); *A61B 5/055* (2013.01)

(58) Field of Classification Search
CPC ............................. H04B 10/116; A61B 5/055
USPC .......................................... 398/118; 600/410
See application file for complete search history.

(56) References Cited

U.S. PATENT DOCUMENTS

| | | | | |
|---|---|---|---|---|
| 6,400,482 B1* | 6/2002 | Lupton | ............... | H04B 10/1143 398/106 |
| 7,123,009 B1* | 10/2006 | Scott | ................... | G01R 33/3621 324/311 |
| 8,971,427 B2* | 3/2015 | Akita | ................... | H04L 27/2657 375/260 |
| 2003/0095263 A1* | 5/2003 | Varshneya | .............. | A61B 5/113 356/477 |
| 2009/0269074 A1* | 10/2009 | Tidhar | ............... | H04B 10/1143 398/130 |
| 2009/0284366 A1* | 11/2009 | Haartsen | ................... | G01S 1/70 340/531 |

(Continued)

FOREIGN PATENT DOCUMENTS

| | | |
|---|---|---|
| DE | 102006037042 A1 | 2/2008 |
| DE | 102011006986 A1 | 10/2012 |

OTHER PUBLICATIONS

"500 Megabit pro Sekunde mit Weisser LED übertragen," Siemens Product Release Reference No. IN20100103-01.

(Continued)

*Primary Examiner* — Ken N Vanderpuye
*Assistant Examiner* — Amritbir Sandhu
(74) *Attorney, Agent, or Firm* — Schiff Hardin LLP

(57) ABSTRACT

In a method for communicating between a first communication device of a magnetic resonance apparatus and a second communication device, in particular one that is mobile and on the patient side, of the magnetic resonance apparatus, a communication technology using visible light is used as the transmission medium for transmission of a useful signal from at least one of the communication devices to the other communication device, in particular from the first communication device to the second communication device.

20 Claims, 2 Drawing Sheets

(56) References Cited

U.S. PATENT DOCUMENTS

| | | | | |
|---|---|---|---|---|
| 2010/0117649 A1* | 5/2010 | Nakanishi | ......... | G01R 33/3692 324/318 |
| 2012/0143040 A1* | 6/2012 | Goswami | ............ | G01R 33/283 600/410 |
| 2013/0011139 A1* | 1/2013 | Hardy | .................. | G06F 19/321 398/79 |
| 2013/0116546 A1 | 5/2013 | Requardt et al. | | |
| 2014/0086590 A1* | 3/2014 | Ganick | ................. | G06Q 30/02 398/118 |
| 2014/0186050 A1* | 7/2014 | Oshima | ............. | H04B 10/1143 398/118 |
| 2014/0199082 A1* | 7/2014 | Iizuka | ................. | H04B 10/116 398/172 |
| 2014/0265920 A1* | 9/2014 | Pederson | .......... | H05B 33/0842 315/294 |
| 2014/0280316 A1* | 9/2014 | Ganick | ............ | G06F 17/30522 707/769 |
| 2014/0309518 A1* | 10/2014 | Sung | .................... | A61B 5/7235 600/410 |
| 2014/0364720 A1* | 12/2014 | Darrow | ................. | A61B 5/748 600/410 |
| 2015/0073269 A1* | 3/2015 | Stopek | .................. | A61B 5/061 600/424 |
| 2015/0104184 A1* | 4/2015 | Jeffrey | .................... | G09C 5/00 398/130 |
| 2015/0147067 A1* | 5/2015 | Ryan | .................... | H04B 10/116 398/118 |
| 2015/0188631 A1* | 7/2015 | Harbers | ............. | H05B 33/0803 398/119 |
| 2015/0190659 A1* | 7/2015 | Kohler | .................... | A61N 7/02 600/411 |
| 2015/0244515 A1* | 8/2015 | Bollenbeck | .......... | G01R 33/283 324/322 |
| 2015/0372754 A1* | 12/2015 | Choi | .................... | H04B 10/116 398/130 |
| 2016/0050531 A1* | 2/2016 | Choi | .................... | H04W 4/027 455/456.2 |
| 2016/0226587 A1* | 8/2016 | Iizuka | ................. | H04B 10/116 |
| 2017/0164908 A1* | 6/2017 | Kimura | ................ | A61B 5/7282 |

OTHER PUBLICATIONS

Brandt-Pearce, "Optical Wireless Communications," Lecture 4, Visible Light Communications, pp. 1-29.

"500 Megabit pro Sekunde mit weuβer LED übertragen," Siemens Global Website (2010).

Brandt-Pearce, Optical Wireless Communications, Lecture 4, Visible Light Communications, pp. 1-29.

* cited by examiner

METHOD FOR COMMUNICATING IN A MAGNETIC RESONANCE APPARATUS AND MAGNETIC RESONANCE APPARATUS OPERATING THEREWITH

BACKGROUND OF THE INVENTION

Field of the Invention

The invention concerns a method for communicating between a first communication device of a magnetic resonance device and a second communication device of the magnetic resonance device, particularly one that is mobile and on the patient side. The invention also relates to such a magnetic resonance apparatus.

Description of the Prior Art and Related Subject Matter

Magnetic resonance devices are widely known in the prior art and are now established as medical imaging devices. For the purpose of imaging, the patient is introduced with a patient couch into a usually cylindrical patient retainer inside a main magnetic unit. The magnetic resonance device is located in a shielded enclosure, which is usually vacated by the operating personnel during the imaging process. A significant amount of noise is generated in the area of the magnetic resonance device during the imaging process. Moreover, the patient retainer of the magnetic resonance device is usually relatively narrow. It is therefore expedient to implement a facility for communicating with the patient, particularly to enable anxious patients to be reassured, and so that instructions can be conveyed to the patient.

Pneumatically operated communication systems have been proposed for this purpose, in which acoustic information is transferred to a patient headset by air pressure modulation. For the return communication it has been proposed, for example, for the patient to use a pneumatically operated call ball; in addition or alternately, microphones may be arranged at the edge of the patient receptacle.

While a call ball is often straightforward to implement, the pneumatic transmission of acoustic information by air pressure modulation requires a complex arrangement of compressed-air hoses, which complicates the layout and operation of the magnetic resonance device. A further disadvantage of transmitting useful signals pneumatically is the poor transmission quality that is achieved.

In the post-published German patent application DE 10 2014 203 368.3 a communication method is proposed that uses radio signals, wherein a carrier signal with a first frequency is emitted by a first communication device of the magnetic resonance apparatus, which is arranged on the basic field magnet side, and this first carrier signal is received on the patient side. There, a second carrier signal is generated with a second frequency, which is different from the first frequency, with a pre-set rational frequency ratio to the first frequency and with a pre-set phase position to the phase of the first carrier signal, onto which the useful signal is modulated, so that the transmit signal thus produced can be returned to the first communication device. In other words, in the second, patient-side communication device, the principle of a phase-locked transponder is used, but the phase-locked transponder signal is not transmitted directly, but is additionally modulated by a useful signal. By continuous transmission of the first carrier signal and of the transmit signal, it is possible for faults in the connection to be detected immediately. Embodiments of the communication method described therein also permit bidirectional communication. The use of radio does however cause problems with regard to approval and/or possible interference/distortions in the magnetic resonance device.

SUMMARY OF THE INVENTION

An object of the invention is to provide an easily implementable, reliable method for transmitting a useful signal in a magnetic resonance apparatus, in particular to a mobile, second communication device on the patient side.

This object is achieved in accordance with the invention by a method of the type described above, but wherein, to facilitate the transmission of a useful signal from at least one of the communication devices to the respective other communication device, in particular from the first communication device to the second communication device, a communication technology that uses visible light as the transmission medium is used.

This light-based communication preferably takes place with regard to the transmission of a useful signal from a fixed first communication device, for example one that is arranged on the side of the basic field magnet of the magnetic resonance device, to a second communication device, in particular one that is mobile and on the patient side, with reverse or even bidirectional transmission of useful signals being possible. A more detailed explanation will be provided below. The second communication device, on the patient side, is arranged inside the patient retainer, for example on the patient couch, at least at the time of the communication.

The invention uses, as wireless communication technology, a communication technology that uses visible light as a transmission medium, as has already been proposed in the prior art, in particular for networking applications in the home and/or office area, and usually referred to by the keyword "visible light communication" (VLC). An illuminating device using at least one LED (light-emitting diode) is preferably used therein to transmit the useful signal, since LEDs are the preferred light sources for the combined purposes of illumination and data communication. In addition to the usual advantages of LEDs are rapid response time, which permits high data rates, and high energy conversion efficiency. White LEDs are preferably used for this purpose, particularly where communication is to be unidirectional. Two predominant technologies exist for white LEDs, namely phosphor-based LEDs and trichromatic LEDs. However particularly where bidirectional communication is to be implemented, it may also be expedient to use colored LEDs with different wavelengths on the side of the first and the second communication device, so that the corresponding transmission channels can then be separated by using suitable optical filters. For example, a green light can be used for illumination of the patient retainer and at the same time for communication to the second communication device, while the second communication device on the patient side uses red LEDs.

However, in general it has been found that—particularly due to the really straightforward implementation of call balls inside the magnetic resonance device and/or the implementation of microphones on the main magnetic unit side—a unidirectional communication link from the first communication device to the second communication device on the patient side is sufficient. In this context the magnetic resonance device expediently has a pneumatically operated call ball as a further unidirectional communication system from the patient to the exterior of the patient retainer and/or a microphone arranged on a main magnetic unit, particularly at the edge of the patient retainer.

Particularly in the context of a unidirectional communication from the first communication device to the second communication device on the patient side, a preferred embodiment of the invention provides for an illuminating device of a patient retainer of the magnetic resonance device to be used as the light source on the side of the first communication device. Such illuminating devices for the patient retainer, which are also known as "in-bore illumination", mainly use white LEDs anyway, which may be arranged, for example, in lines or form light strips in a cladding of the patient retainer. This means that an existing light source is used, which illuminates the patient retainer evenly and safely, with little or no external light—which may cause additional noise—being present.

Other general advantages of using VLC technology are that no radio license is required and no space-consuming antennas need to be implemented. Particularly if an illuminating device is used for the patient retainer of the magnetic resonance device, the local, barely distorted lighting conditions are thus optimally exploited, which—due to the existing light source—offers a transmission option which is easy to implement, fail-safe and reliable.

In order to receive the light used for transmission of the useful signal, a light receiving device using a photodetector and/or having an optical concentrator and/or optical filter may be used. Embodiments known from VLC technology may be used for this, the use of an optical concentrator and an optical filter having an advantageous effect on the signal-to-noise ratio (SNR). An optical filter is particularly expedient where white LEDs are used, which combine light emitted at discrete wavelengths.

A carrier signal applied as an amplitude modulation for the brightness of the light can be used on the side of the transmitting, in particular the first, communication device. In order to define the brightness or intensity of the light emitted from the light source, preferably the illuminating device for the patient retainer, the LEDs are usually sent a control signal of a defined amplitude specifying the required brightness. The brightness of the light is therefore easily varied by the carrier signal; this is imperceptible to an observer but facilitates the transmission of the useful signal, which is expediently modulated to the carrier signal. This carrier signal preferably has a frequency that is lower than 10 MHz, in particular lower than 3 MHz. A preferred frequency may be 2.5 MHz, for example. Such low frequencies do not generate any interference signals relevant for magnetic resonance imaging. Interference problems, particularly with regard to the electrical power supply to the light source, particularly the LEDs, do not occur.

In another embodiment of the invention, the useful signal is introduced into the light in analog form by angle modulation of the carrier signal. The brightness of the light is thus first modulated with the carrier signal, with the carrier signal coding the actual low-frequency information—the useful signal which is, in particular, an acoustic signal (voice, music)—in the form of an angle modulation. The angle modulation offers the advantage that it is immune to amplitude distortions due to a non-linear transmission characteristic of the light source, in particular of the LEDs. The advantage of analog angle modulation, in particular an analog phase modulation, a frequency modulation of course also being conceivable, is that it enables a narrow-band modulation to occur, which also ensures that there is very little effect on other components of the magnetic resonance device, in particular with regard to the magnetic resonance imaging. A further advantage of the analog brightness modulation by means of the carrier signal that carries the useful information in the form of an angle modulation, is that no digital signal processing is necessary on the side of the second, patient-side communication device. The angle modulation ensures extensive immunity against non-linearities in the light source characteristic, which has LEDs. The angle modulation also permits highly efficient implementation, particularly since no linear amplifiers are needed, but strongly non-linear amplifiers can be used.

Furthermore, distortions can be reduced the carrier signal being generated phase-locked to a basic pulse signal of the magnetic resonance device. This means that the frequency of the carrier signal corresponds to a multiplication of the frequency of the basic pulse signal by a rational factor, with a fixed phase relationship being specified. This permits the receiving electronics of the receiving communication device, in particular the second communication device, to be designed for detection of an internal pulse signal phase-locked to the carrier signal. The internal pulse signal of the receiving communication device, in particular of the second communication device, is also hereby phase-locked to the basic pulse of the magnetic resonance device, without the basic pulse signal of the magnetic resonance device of the receiving communication device having to be supplied in another way. Ultimately, therefore, a phase-locked loop (PLL) is implemented, so that the conveyance of the carrier signal on the side of the receiving communication device results in a kind of synchronous demodulator, by which distortions and interference are further avoided, since the internal pulse signal of the receiving communication device is coupled to the basic pulse signal of the magnetic resonance device. In this way a high signal-to-noise ratio and/or high sensitivity can be achieved on the side of the light receiving device.

Inside the receiving device, i.e. the second communication device, by using the internal pulse signal the receiving signal is expediently converted to an intermediate frequency, which is lower, so that amplification can take place on the intermediate frequency, which further reduces distortions and interference.

Overall, therefore, it is precisely the interaction of the use of the carrier signal as brightness variation, to which the useful signal is modulated by angle modulation, at rather low frequencies of the carrier signal, together with the phase-locked coupling of the carrier signal and the internal pulse signal of the receiving communication device, that facilitates a transmitter-receiver architecture in which interference signals relevant for magnetic resonance imaging are minimized, or in particular are even eliminated completely.

It should be noted that the control signal via which the light source is controlled does of course have a direct component, via which the optimal operating point of the light source is set, thus for example a required brightness level within the patient retainer for use of an illuminating device for the patient retainer. For example, a transmit signal can be first generated by angle modulation of the useful signal to the carrier signal, which is fed to a modulatable power source, which receives a brightness signal for controlling the brightness and thus generates the control signal for the light source, in particular an LED array.

The receiving electronics of the receiving communication device, in particular the second communication device, are expediently shielded with a radio-frequency shield. The receiving, in particular the second, communication device does not require a radio-frequency interface and can therefore be hermetically shielded, so that only the light inlet aperture for the light receiving device and possibly a low-frequency interface is required, to which a headset for the patient may be connected, for example.

A communication device integrated in and/or connected to a patient headset is therefore preferably provided as the second communication device, wherein the aforementioned low-frequency interface to the second communication device may be provided for connecting the headset, for example. It is therefore expedient for the useful signal to be acoustic information, which—as explained above—is preferably transmitted in analog form, in order to permit a narrow-band phase modulation or narrow-band angle modulation in general. Overall, a VLC-headset device may be implemented by the second communication device and the headset, and can easily be retrofitted to already installed magnetic resonance scanners, which have an illuminating device for the patient retainer, which illuminating device uses LEDs.

In addition to the method, the invention also concerns a magnetic resonance apparatus, having a communication system with a first communication device and a second communication device, in particular one that is mobile and on the patient side, with a communication system being designed to implement the inventive method. All embodiments with regard to the inventive method apply analogously to the inventive magnetic resonance apparatus, so the aforementioned advantages can also be obtained.

The communication takes place from the first communication device to the second communication device arranged inside the patient receptacle, at least during the period of communication, wherein the first communication device can thus have a light source which is preferably designed as an illuminating device for the patient retainer of the magnetic resonance device. The first communication device moreover has a control circuit, which generates a control signal for the light source in the described manner, in particular a control signal having a direct component (component that is constant in time) for controlling the brightness, which has as the brightness variation the carrier signal to which the useful signal is modulated by analog angle modulation. A light receiving device is then provided on the side of the second communication device, which light receiving device in turn follows a control circuit implementing the receiving electronics, which control circuit extracts the useful signal from the received light signal, in particular as a synchronous demodulator, which uses an internal pulse signal, which is coupled in a phase-locked way to a basic pulse signal of the magnetic resonance device upon transmission of the carrier signal.

DESCRIPTION OF THE PREFERRED EMBODIMENTS

Figure 1:
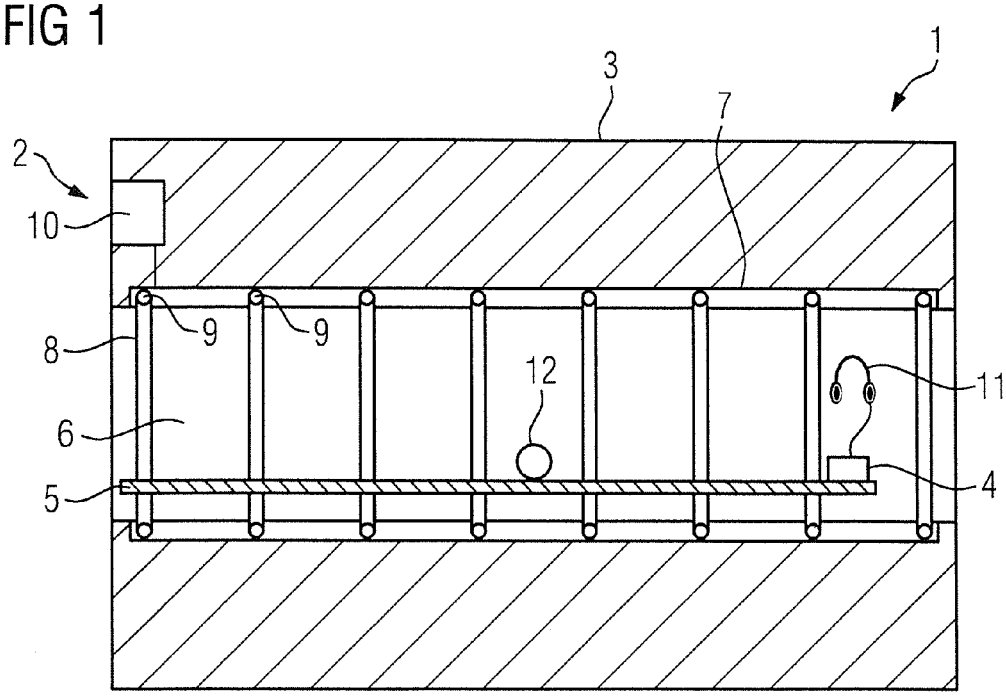
FIG. 1 schematically illustrates an inventive magnetic resonance device.

FIG. 1 schematically shows a scanner 1 of an inventive magnetic resonance apparatus, which has a communication system with a first communication device 2, which is implemented in the main magnetic unit 3, and a second communication device 4, which is provided at the patient bed 5. This diagram shows a basic cross-section through the magnetic resonance device 1, from which the basic field magnet 3 and the patient receptacle 6 are thus easily visible. For simplicity this diagram shows only the components relevant for the present invention; the other construction of the magnetic resonance device 1, with gradient coils, radio-frequency coils, basic field magnet, etc. is widely known in the art.

Integrated into the cladding of the patient receptacle 6 is an illuminating device 7 for the latter, which is designed in this case as a plurality of circumferential illuminating rings 8 with white light emitting LEDs 9. Illuminating devices 7 in which the LED arrays extend longitudinally along the patient receptacle 6 or are otherwise arranged, are of course also possible. The illuminating device 7 illuminates the patient receptacle 6 evenly with white light. This light from the illuminating device 7 is now used as a transmission medium for transmitting a useful signal to the second communication device 4, for which purpose the first communication device 2 also has a control circuit 10 in addition to the illuminating device 7 as the light source, which control circuit 10 generates a control signal in a manner explained in greater detail with reference to FIG. 2, so that a transmit signal is communicated by the LEDs 9. This is received by a light receiving device of the second communication device 4 and processed further as a receive signal in a control device located therein, in order to extract the useful signal. The useful signal in this case is an acoustic signal, for example comprising voice and/or music, which is emitted to a headset 11 connected to the second communication device.

Also indicated at the patient bed 5 is a pneumatically operated call ball 12 for the patient; it should be noted here that embodiments are also possible in which the communication that takes place from the first communication device 2 to the second communication device 4 is not unidirectional, but bidirectional, which is also possible for example using light-differentiated wavelengths, wherein the principles still to be described below for ensuring that the useful signal is transmitted as robustly and with as little distortion as possible can of course also be transferred to bidirectional communication.

Figure 2:
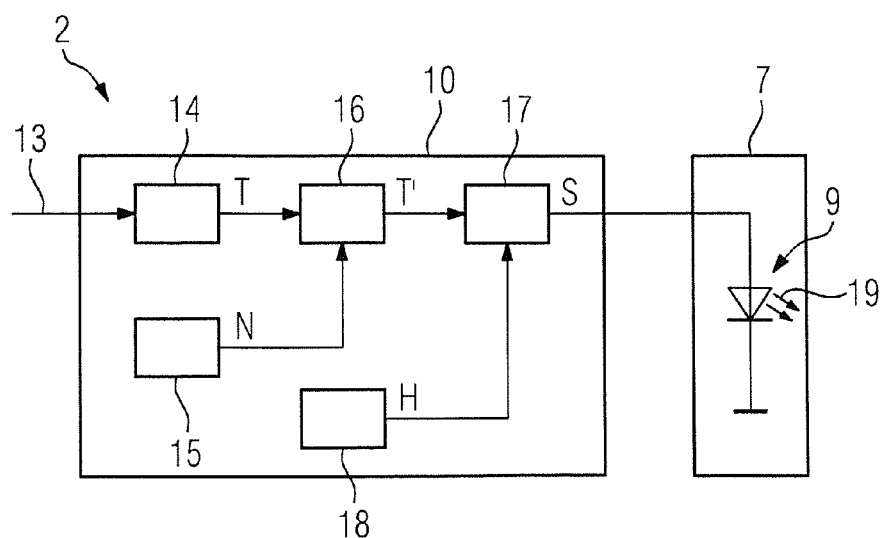
FIG. 2 shows the construction of the first communication device.

FIG. 2 now shows the construction of the first communication device 2 in greater detail in a further schematic diagram. The main components of the first communication device 2 are the control circuit 10 and the light source, i.e. the LEDs 9 of the illuminating device 7.

From a further control circuit of the magnetic resonance device 1, the control circuit 10 receives a basic pulse signal as indicated by the arrow 13, which is used in a carrier signal generation unit 14 to generate a carrier signal T which is phase-locked to the basic pulse signal of the magnetic resonance device 1, at a frequency of 2.5 MHz. This means that the frequency of the carrier signal, 2.5 MHz, is produced by multiplication with a rational factor from the frequency of the basic pulse signal of the magnetic resonance device 1 and is phase-locked to it. A useful-signal source 15 delivers the useful signal N, which is also usually fed to the control circuit 10 from the exterior, to a phase modulator 16, which adds the useful signal N to the carrier signal T by analog narrow-band phase modulation. A phase-modulated carrier signal T' is produced, which is forwarded to a modulatable power source 17. To this latter, a brightness value H is supplied by a brightness control unit 18, the power source 17 generating a control signal S for the LEDs 9 from the phase-modulated carrier signal T' and the brightness value H, which control signal contains a suitable direct component for the required brightness value H, in which the intensity of the LEDs 9 can then easily be varied with the phase-modulated carrier signal T' in a way that is imperceptible for the observer.

The LEDs 9 of the illuminating device 7 then emit light 19 as indicated by the arrows.

Figure 3:
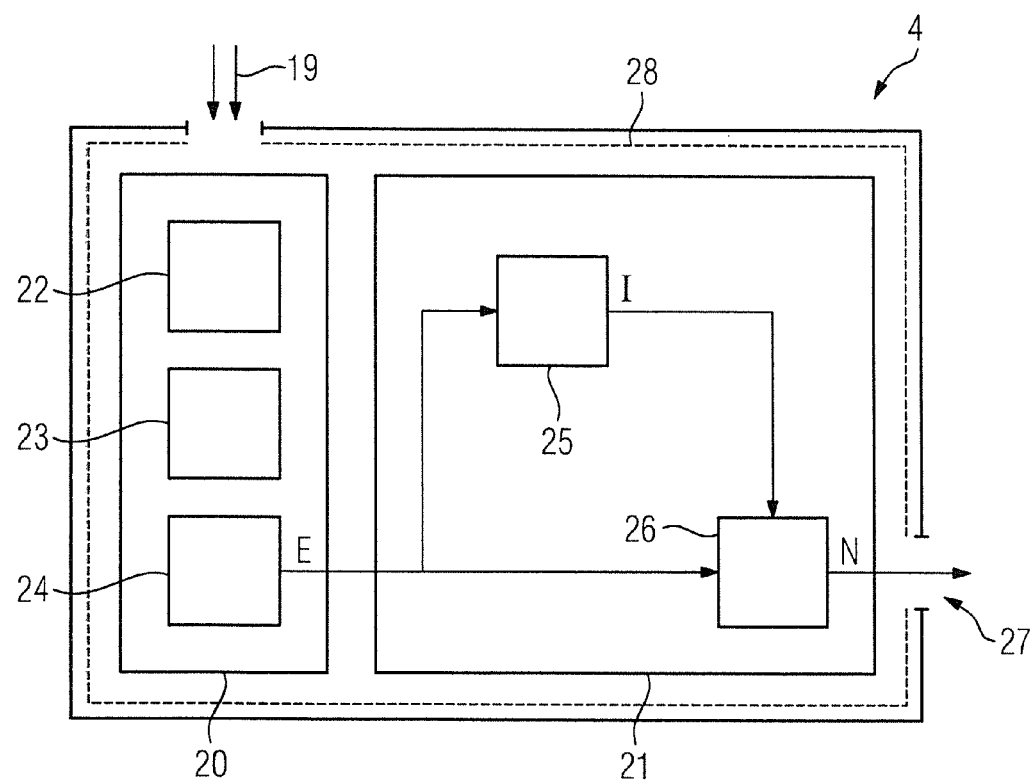
FIG. 3 shows the construction of the second communication device.

FIG. 3 shows a corresponding schematic diagram of the second communication device 4, which—in addition to the light receiving device 20—likewise, as already mentioned, has a control device 21 which implements the receiving electronics. The light 19 falls through a light inlet aperture onto the light receiving device 20, which has an optical concentrator 22, an optical filter 23 for the discrete wavelengths emitted by the LEDs 9, and a photodetector 24. By amplification of the light 19 in the optical concentrator 22 and selection of the light 19 emitted by the LEDs 9 by means of the optical filter 23, noise effects are reduced and the signal-to-noise ratio is increased.

Since the direct component is already removed on the side of the photodetector 24, finally the phase-modulated carrier signal T' is essentially received in turn as the receive signal E and forwarded to the control device 21. The receive signal E is used there firstly to generate an internal pulse signal I in a pulse signal generation unit 25, which has a frequency which is produced by multiplication by a rational factor from the frequency of the carrier signal T and is defined out of phase to the carrier signal T. The internal pulse signal I is thus phase-locked to the carrier signal T and thus to the basic pulse signal of the magnetic resonance device 1. In this way the demodulator 26, to which the receive signal E is also supplied, functions as a synchronous demodulator. The demodulator 26 again receives the useful signal N, which can be supplied to the headset 11 by a low-frequency interface 27. Further electronic components can also be used to convert signals to intermediate frequencies at which they can be further processed; furthermore, amplifiers etc. are of course usually provided, in particular on the side of the control device 21, but these are omitted here for the sake of clarity.

Other electronic components can of course also be added as components of the receiving electronics or control circuit 21 of the second communication device or of the control circuit 10 of the first communication device 2, which for example ensure improvements to the signal quality, and so forth. After the useful signal N has been transmitted in analog form, it can be directly used as an acoustic signal in the headset 14.

The second communication device 4, which can also be integrated in the headset 11, evidently does not have a radio-frequency interface. Its receiving electronics (control device 21) are shielded from the exterior together with the light receiving device 20 by a radio-frequency shield 28.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for communicating an information signal to an interior of a patient receptacle inside of a magnetic resonance (MR) data acquisition scanner of an MR apparatus, said MR data acquisition scanner having illumination lighting inside of said patient receptacle that emits light that illuminates the overall interior of said patient receptacle, said method comprising:
   providing an input information signal to a control circuit situated outside of said patient receptacle and, in said control circuit, generating an electrical control signal that represents information in said input information signal;
   communicating said control signal to said illumination lighting inside of said patient receptacle, and operating said illumination lighting with said control signal to embody said information in the light emitted by said illumination lighting;
   detecting said light embodying said information with a light detector circuit situated in the interior of said patient receptacle and, in said light detector circuit, recovering said information from the detected light and converting said information into an output information signal; and
   communicating said output information signal to an acoustic signal generator situated in the interior of said patient receptacle and, in said acoustic signal generator, converting said information signal into an acoustic signal, and emitting said acoustic signal from said acoustic signal generator in the interior of the patient receptacle.

2. A method as claimed in claim 1 comprising emitting visible light from said illuminating lighting inside of said patient receptacle.

3. A method as claimed in claim 2 comprising operating said illuminating lighting with said control signal to invisibly embody said information in said visible light.

4. A method as claimed in claim 2 wherein said visible light comprises a carrier signal, and wherein said method comprises, in said control circuit, embodying said information in said carrier signal of said visible light by modulating a brightness amplitude of said carrier signal.

5. A method as claimed in claim 4 comprising, in said control circuit, modulating said brightness amplitude using analog angle modulation of said carrier signal.

6. A method as claimed in claim 1 comprising operating said illumination lighting from said control circuit with a carrier signal that is phase-locked to a basic pulse signal of the magnetic resonance apparatus.

7. A method as claimed in claim 6 wherein said light detector circuit recovers said information from the detected light using an internal pulse signal, in said light detector circuit, that is phase-locked to said carrier signal.

8. A method as claimed in claim 1 comprising using a patient headset, adapted to be worn by a patient in said MR data acquisition scanner, as said acoustic signal generator.

9. A method as claimed in claim 1 comprising using a hand-held mobile communication device as said acoustic signal generator.

10. A magnetic resonance (MR) apparatus comprising:
   an MR data acquisition scanner having a patient receptacle therein, said MR data acquisition scanner comprising illumination lighting inside of said patient receptacle that emits light that illuminates an overall interior of said patient receptacle;
   a control circuit situated outside of said patient receptacle, said control circuit being provided with input information and said control circuit generating an electrical control signal that represents information in said input information signal;
   said control circuit being connected to said illumination lighting and operating said illumination lighting with said control signal to embody said information in the light emitted by said illumination lighting;
   a light detector circuit situated in the interior of said patient receptacle that detects said light embodying said information and that recovers said information from the detected light and converts said information into an output information signal; and
   an acoustic signal generator situated in the interior of said patient receptacle to which said output information is provided by light detector circuit, said acoustic signal generator converting said information signal into an acoustic signal, and emitting said acoustic signal from said acoustic signal generator in the interior of the patient receptacle.

11. An apparatus as claimed in claim 10 wherein said illuminating lighting emits visible light inside of said patient receptacle.

12. An apparatus as claimed in claim 11 wherein said control circuit operates said illuminating lighting with said control signal to invisibly embody said information in said visible light.

13. An apparatus as claimed in claim 11 wherein said visible light comprises a carrier signal, and wherein said control circuit embodies said information in said carrier signal of said visible light by modulating a brightness amplitude of said carrier signal.

14. An apparatus as claimed in claim 13 wherein said control circuit modulates said brightness amplitude using analog angle modulation of said carrier signal.

15. An apparatus as claimed in claim 13 wherein said control circuit operates said illumination lighting with a carrier signal that is phase-locked to a basic pulse signal of the magnetic resonance apparatus.

16. An apparatus as claimed in claim 15 wherein said light detector circuit recovers said information from the detected light using an internal pulse signal, in said light detector circuit that is phase-locked to said carrier signal.

17. An apparatus as claimed in claim 10 wherein said acoustic signal generator is a patient headset, adapted to be worn by a patient in said MR data acquisition scanner.

18. An apparatus as claimed in claim 10 wherein said illumination lighting is a light emitting diode (LED) illuminator.

19. An apparatus as claimed in 10 wherein said light detector circuit comprises a light receiver selected from the group consisting of a photo detector, an optical concentrator, and an optical filter.

20. An apparatus as claimed in claim 10 wherein said MR data acquisition scanner produces radio-frequency (RF) signals during operation thereof, and wherein said light detector circuit comprises an RF shield that shields at least a portion of said light detector circuit from said RF signals.

* * * * *